United States Patent
Enomoto et al.

(10) Patent No.: US 10,335,111 B2
(45) Date of Patent: Jul. 2, 2019

(54) ELECTRONIC CASSETTE SYSTEM AND ELECTRONIC CASSETTE

(71) Applicant: FUJIFILM Corporation, Tokyo (JP)

(72) Inventors: Jun Enomoto, Ashigarakami-gun (JP); Makoto Kitada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 104 days.

(21) Appl. No.: 14/839,483

(22) Filed: Aug. 28, 2015

(65) Prior Publication Data
US 2016/0081649 A1 Mar. 24, 2016

(30) Foreign Application Priority Data
Sep. 22, 2014 (JP) .................................. 2014-193133

(51) Int. Cl.
*A61B 6/00* (2006.01)
*H01R 13/73* (2006.01)

(52) U.S. Cl.
CPC .............. *A61B 6/56* (2013.01); *A61B 6/4283* (2013.01); *H01R 13/73* (2013.01)

(58) Field of Classification Search
CPC ....... A61B 6/4283; A61B 6/56; A61B 6/4233; A61B 6/566; H01R 23/02; H01R 24/60; H01R 24/62
See application file for complete search history.

(56) References Cited

U.S. PATENT DOCUMENTS

| | | | | |
|---|---|---|---|---|
| 6,638,099 B2 * | 10/2003 | Nakamura | ........... | H01R 13/641 439/489 |
| 8,033,871 B2 * | 10/2011 | Pocrass | .................. | H01R 24/64 439/676 |
| 8,172,461 B2 * | 5/2012 | Liu | ....................... | A61B 6/4283 378/114 |

(Continued)

FOREIGN PATENT DOCUMENTS

| | | |
|---|---|---|
| JP | 2004-177251 A | 6/2004 |
| JP | 3137548 U | 11/2007 |

(Continued)

OTHER PUBLICATIONS

Japanese Office Action and English translation, dated May 24, 2017, for corresponding Japanese Application No. 2014-193133.

(Continued)

*Primary Examiner* — David J Makiya
*Assistant Examiner* — Soorena Kefayati
(74) *Attorney, Agent, or Firm* — Birch, Stewart, Kolasch & Birch, LLP

(57) ABSTRACT

A center position of a female connector is located near to a rear surface of a housing compared with a center position of the housing in a thickness direction of the housing of an electronic cassette. An inclined surface, which is inclined relative to a side surface and the rear surface of the housing, is formed between the side surface and the rear surface. The female connector is formed on the inclined surface. Therefore, it is possible to attach an outer grid provided with a (Continued)

longer side panel to the housing, in comparison with the case where the center position of the female connector is made coincident with the center position of the housing in the thickness direction of the housing, without requiring any processing.

8 Claims, 9 Drawing Sheets

(56) References Cited

U.S. PATENT DOCUMENTS

| | | | | |
|---|---|---|---|---|
| 8,265,225 B2* | 9/2012 | Nishino | ............... | A61B 6/4283 378/102 |
| 8,324,585 B2* | 12/2012 | McBroom | ............ | A61B 6/4233 250/370.09 |
| 8,704,188 B2* | 4/2014 | Kitano | ................ | A61B 6/548 250/370.09 |
| 8,956,045 B2* | 2/2015 | Tajima | ................. | A61B 6/4283 378/145 |
| 9,101,317 B2* | 8/2015 | Kobayashi | ............ | A61B 6/4233 |
| 9,414,802 B2* | 8/2016 | Urbon | ................. | A61B 6/4283 |
| 9,543,694 B2* | 1/2017 | Tagawa | ................. | H01R 13/62 |
| 9,855,017 B2* | 1/2018 | Wojcik | ................. | A61B 6/4233 |
| 2008/0165931 A1* | 7/2008 | Luusua | ................. | A61B 6/032 378/154 |
| 2009/0190718 A1* | 7/2009 | Fan | ...................... | A61B 6/4283 378/102 |
| 2010/0148081 A1* | 6/2010 | Yoshimi | ................ | A61B 6/00 250/370.08 |
| 2011/0248173 A1* | 10/2011 | Ogura | ................ | A61B 6/4283 250/361 R |
| 2012/0002784 A1* | 1/2012 | Nishino | ............... | A61B 6/4216 378/62 |
| 2012/0281817 A1* | 11/2012 | McBroom | ............ | A61B 6/4283 378/204 |
| 2012/0300413 A1* | 11/2012 | Iida | ...................... | A61B 6/4233 361/728 |
| 2013/0083898 A1* | 4/2013 | Tajima | ................. | A61B 6/4283 378/97 |
| 2013/0136235 A1* | 5/2013 | Liu | ...................... | A61B 6/4233 378/98 |
| 2013/0214157 A1* | 8/2013 | Kitano | ................. | A61B 6/4283 250/336.1 |
| 2014/0211921 A1* | 7/2014 | Bandis | .................... | H01M 2/08 378/91 |
| 2015/0063550 A1* | 3/2015 | Wojcik | ................. | A61B 6/4233 378/189 |
| 2015/0366524 A1* | 12/2015 | Suzuki | ................. | A61B 6/4283 378/189 |
| 2016/0029984 A1* | 2/2016 | Jang | ..................... | A61B 6/4429 378/189 |

FOREIGN PATENT DOCUMENTS

| | | |
|---|---|---|
| JP | 3144690 U | 8/2008 |
| JP | 2010-115362 A | 5/2010 |
| JP | 2010-262297 A | 11/2010 |
| JP | 2012-181238 A | 9/2012 |
| JP | 2012-208334 A | 10/2012 |

OTHER PUBLICATIONS

Japanese Decision of Refusal, dated Dec. 7, 2017, for corresponding Japanese Application No. 2014-193133, with an English machine translation.

* cited by examiner

ELECTRONIC CASSETTE SYSTEM AND ELECTRONIC CASSETTE

CROSS-REFERENCE TO RELATED APPLICATIONS

The present application claims priority under 35 U.S.C. § 119 to Japanese Patent Application No. 2014-193133, filed Sep. 22, 2014. The above application is hereby expressly incorporated by reference, in its entirety, into the present application.

BACKGROUND OF THE INVENTION

1. Field of the Invention

The present invention relates to an electronic cassette system and an electronic cassette for use in radiography.

2. Description Related to the Prior Art

An electronic cassette has been widely used in medical radiography, for example, in X-ray photography. An electronic cassette system includes an electronic cassette. The electronic cassette is a portable X-ray image detector provided with an built-in image detector (also referred to as flat panel detector (FPD)) for detecting an X-ray image of a subject such as a patient inside a housing having a front surface on which X-rays are incident, a rear surface facing the front surface, and four side surfaces.

The electronic cassette is provided with a female connector for connecting the electronic cassette to an external device such as a control device for controlling operation of the electronic cassette. A male connector is connected to the female connector.

Japanese Patent Laid-Open Publication No. 2012-208334 discloses an electronic cassette in which a female connector (corresponding to "socket 34" in Japanese Patent Laid-Open Publication No. 2012-208334) is formed on a side surface of a housing (see FIG. 3 in Japanese Patent Laid-Open Publication No. 2012-208334). According to Japanese Patent Laid-Open Publication No. 2012-208334, in a thickness direction of the housing perpendicular to a front surface and a rear surface of the housing, a center position of the female connector is made coincident with a center position of the thickness of the housing.

Incidentally, in X-ray photography, since scattered rays are generated upon transmission of X-rays through a subject, a grid for removing the scattered rays is used in some cases. There is a grid detachably attached to a housing externally (hereinafter referred to as external grid) (see Utility Model Registration No. 3137548 and Utility Model Registration No. 3144690).

The external grid consists of a grid body and a holding frame for holding the grid body. The grid body is attached to the holding frame. The holding frame has a top panel for covering the front surface of the housing, and a side panel which is provided to an edge of the top panel and extends in a direction from a front-surface side of the housing toward a rear-surface side thereof so as to cover part of a side surface of the housing. The side panel has a length enough to reach the center position of the thickness of the housing so as to facilitate positioning of the outer grid relative to the housing.

In the case where the center position of the female connector in the thickness direction of the housing is made coincident with the center position of the thickness of the housing as disclosed in Japanese Patent Laid-Open Publication No. 2012-208334, when the outer grid is attached to the housing, due to the length of the side panel, the female connector is covered by the side panel, and thus the male connector cannot be connected to the female connector in some cases. Accordingly, there is a limit for the kind of the usable outer grids.

In the case where the female connector is covered by the side panel, the female connector becomes usable at any rate by processing a portion of the side panel covering the female connector, for example, by cutting out of the portion of the side panel covering the female connector. However, such processing is troublesome. Additionally, the strength of the outer grid may be deteriorated in some cases.

SUMMARY OF THE INVENTION

In view of the foregoing, an object of the present invention is to provide an electronic cassette system and an electronic cassette capable of using a greater variety of outer grids without subjecting the outer grids to troublesome processing.

To achieve the above object of the present invention, an electronic cassette system of the present invention includes an electronic cassette having an image detector and a housing for housing the image detector, a female connector disposed in the housing, and a male connector to be connected to the female connector. The image detector detects a radiation image of a subject based on radiation having been transmitted through the subject. The housing has a front surface on which the radiation is incident, a rear surface facing the front surface, and four side surfaces. The male connector extends from a side-surface side of the housing in a direction parallel to the front surface and the rear surface of the housing. A center position of the female connector is located near to the rear surface of the housing compared with a center position of the housing in a thickness direction of the housing perpendicular to the front surface and the rear surface.

The male connector preferably includes a main section to which one end of a cable for connecting the electronic cassette to another device in a wired manner is connected, and a terminal section having a terminal which is fit into the female connector to establish an electrical connection between the electronic cassette and the device. In this case, preferably, the terminal section is thinner than the main section in the thickness direction of the housing, and a center position of the terminal section is located near to the rear surface of the housing compared with a center position of the main section in the thickness direction of the housing. Further, the main section and the terminal section are preferably connected to each other by a flat surface on a rear-surface side of the housing.

Preferably, a gap is provided between an end surface which is formed between the main section and the terminal section and a surface of the housing which faces the end surface upon connection of the male connector to the female connector by fitting the terminal section into the female connector.

The housing preferably has an inclined surface which is formed at least between one of the side surfaces and the rear surface and inclined relative to the one of the side surfaces and the rear surface. In this case, the female connector is preferably formed on the inclined surface.

It is preferable that the electronic cassette system further includes an outer grid detachably attached to the housing externally, for removing scattered rays generated upon transmission of the radiation through the subject.

The outer grid preferably includes a top panel for covering the front surface of the housing, and a side panel which is provided to an edge of the top panel and extends in a direction from a front-surface side to a rear-surface side of the housing so as to cover part of the side surface of the housing.

In the case where a gap is provided between an end surface which is formed between the main section and the terminal section and a surface of the housing which faces the end surface upon connection of the male connector to the female connector by fitting the terminal section into the female connector, the gap preferably has a size capable of receiving the side plate.

Further, an electronic cassette of the present invention includes an image detector for detecting a radiation image of a subject based on radiation having been transmitted through the subject, a housing for housing the image detector, and a female connector disposed in the housing. The housing has a front surface on which the radiation is incident, a rear surface facing the front surface, and four side surfaces. The female connector is connected to a male connector extending from a side-surface side of the housing in a direction parallel to the front surface and the rear surface of the housing. A center position of the female connector is located near to the rear surface of the housing compared with a center position of the housing in a thickness direction of the housing perpendicular to the front surface and the rear surface.

According to the present invention, the center position of the female connector is located near to the rear surface of the housing compared with the center position of the housing in the thickness direction of the housing. Therefore, it is possible to provide the electronic cassette system and an electronic cassette capable of using a greater variety of outer grids without subjecting the outer grids to troublesome processing.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
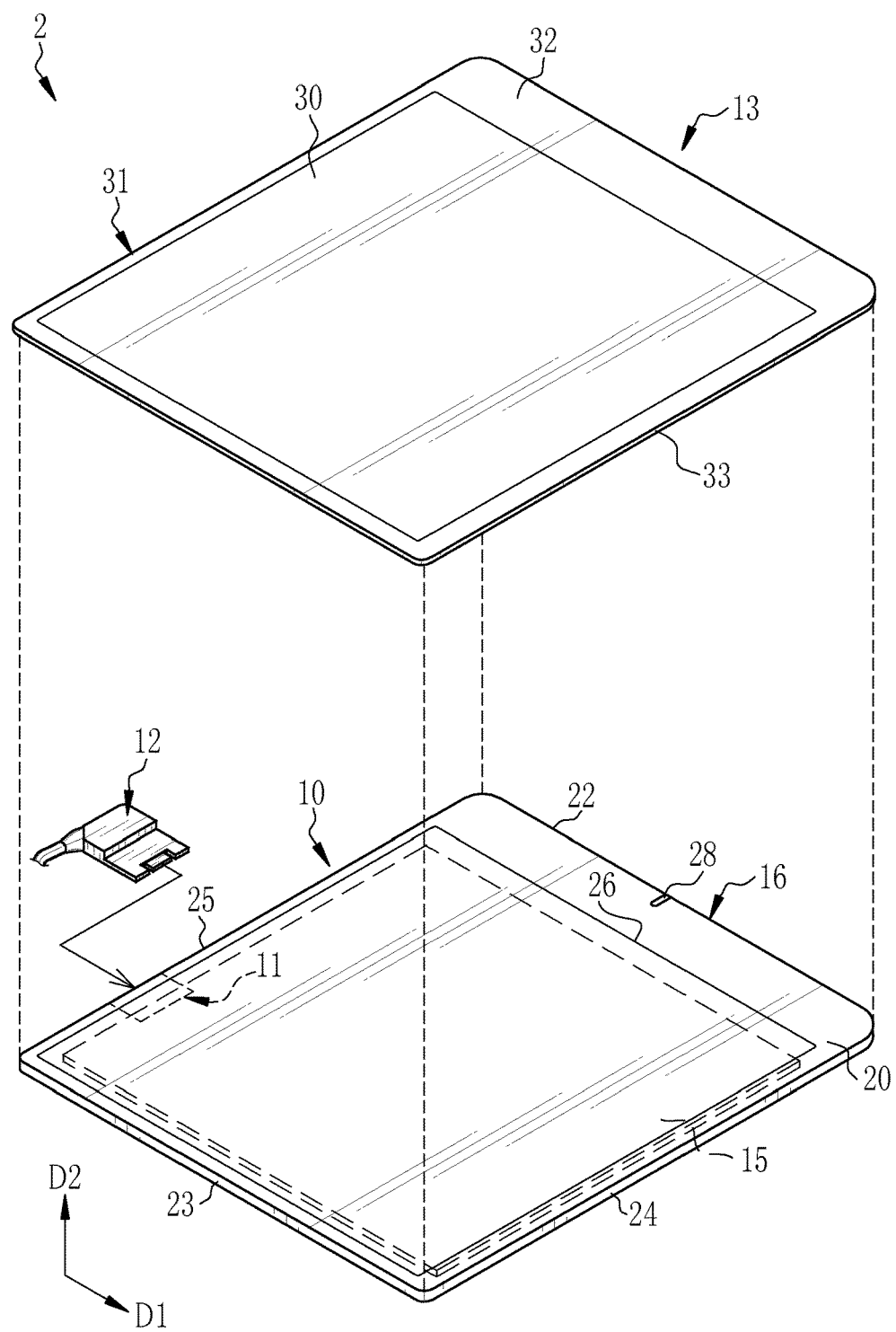
FIG. 1 is a perspective view illustrating an external appearance of an electronic cassette system.

In FIG. 1, an electronic cassette system 2 is used for medical X-ray photography, for example, and consists of an electronic cassette 10, a male connector 12 to be connected to a female connector disposed in the electronic cassette 10, and an outer grid 13.

The electronic cassette 10 consists of an image detector 15 and a portable housing 16 for housing the image detector 15. The image detector 15 detects an X-ray image of a subject based on X-rays having been transmitted through the subject.

As well known, the image detector 15 includes a scintillator (phosphor) for converting incident X-rays into visible light beams, and a thin film transistor (TFT) active matrix substrate having a plurality of pixels each of which accumulates charge corresponding to the visible light beams from the scintillator. The housing 16 incorporates not only the image detector 15 but also a gate driver, a signal processing circuit, a control section, and the like. The gate driver supplies a gate pulse to a gate of the TFT to switch the TFT. The signal processing circuit converts the charge accumulated in each of the pixels into a voltage signal representing an X-ray image, and outputs the voltage signal. The control section controls operation of each of the gate driver and the signal processing circuit.

The housing 16 consists of a front surface 20 on which the X-rays are incident, a rear surface 21 facing the front surface 20 (see FIG. 2), and four side surfaces 22, 23, 24, and 25, so as to have a rectangular parallelepiped shape. The housing 16 is made of electrically-conductive resin, for example. The housing 16 also functions as an electromagnetic shield for preventing electromagnetic noise from entering the electronic cassette 10 and preventing electromagnetic noise from being emitted from the electronic cassette 10 to the outside. The housing 16 has a size compliant with the ISO (International Organization for Standardization) 4090: 2001 which is substantially the same as the size of each of a film cassette, an IP (Imaging Plate) cassette, and a CR (Computed Radiography) cassette, for example.

The electronic cassette 10 is set to be attachable to and detachable from a holder of an upright radiographic stand or a supine radiographic stand, such that the electronic cassette 10 is held in a posture in which an X-ray source for irradiating X-rays and the front surface 20 of the housing 16 face each other. Further, the electronic cassette 10 is used alone for a subject lying on a bed or a subject who cannot move on his/her own such as an aged person or an emergency patient in some cases, in addition to being set to the holder of the upright radiographic stand or the supine radiographic stand. Furthermore, in the case where the housing 16 has substantially the same size as that of each of the film cassette, the IP cassette, and the CR cassette, the electronic cassette 10 can be attached to an existing radiographic stand for these cassettes.

A rectangular opening is formed on the front surface 20 of the housing 16. A transmission plate 26 is attached to the opening. A protection film 27 (see FIG. 6) made of a resin, through which the X-rays are transmitted, is adhered to a surface of the transmission plate 26. This allows the front surface 20 to be a flat surface. The transmission plate 26 is made of a carbon material which is lightweight, highly rigid, and extremely permeable to the X-rays. Additionally, an indicator 28 such as an LED (Light Emitting Diode) is disposed on the front surface 20 at the side of the side surface 22 of the housing 16 so as to indicate power on/off of the electronic cassette 10.

Figure 6:
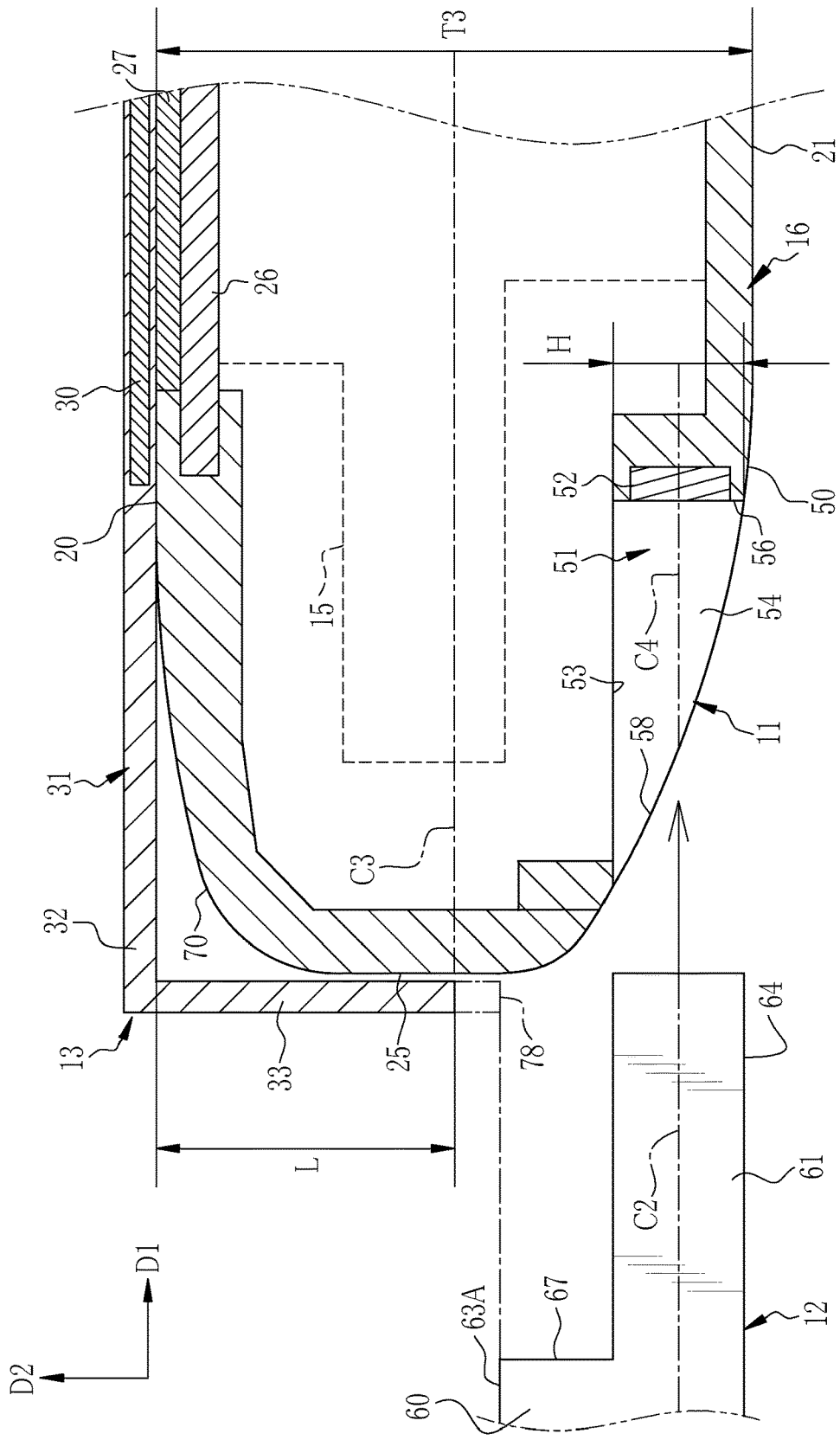
FIG. 6 is a cross-sectional view of each of the electronic cassette and an outer grid taken along a line VI-VI of FIG. 3.

The outer grid 13 is detachably attached to the housing 16 externally in order to remove scattered rays generated upon transmission of X-rays through the subject (see FIG. 6). The outer grid 13 consists of a rectangular grid body 30 and a holding frame 31 for holding the grid body 30. The grid body 30 is slightly larger than the transmission plate 26 so as to cover the entire transmission plate 26 when the outer grid 13 is attached to the housing 16. Further, the holding frame 31 is made of a metal material such as stainless, and slightly larger than the housing 16.

The holding frame 31 has a top panel 32 and a side panel 33. The top panel 32 has a rectangular opening to which the grid body 30 is attached. When the outer grid 13 is attached to the housing 16, the top panel 32 and the grid body 30 cover the front surface 20 of the housing 16. The side panel 33 is provided to an edge of the top panel 32, and extends in a direction from the front surface 20 to the rear surface 21. Incidentally, although not shown in the drawing, the holding frame 31 is provided with a well-known dropping prevention/dropping prevention releasing mechanism. The dropping prevention/dropping prevention releasing mechanism fixes the outer grid 13 to the housing 16 so as to prevent the outer grid 13 from being dropped, and releases the dropping prevention.

Figure 2:
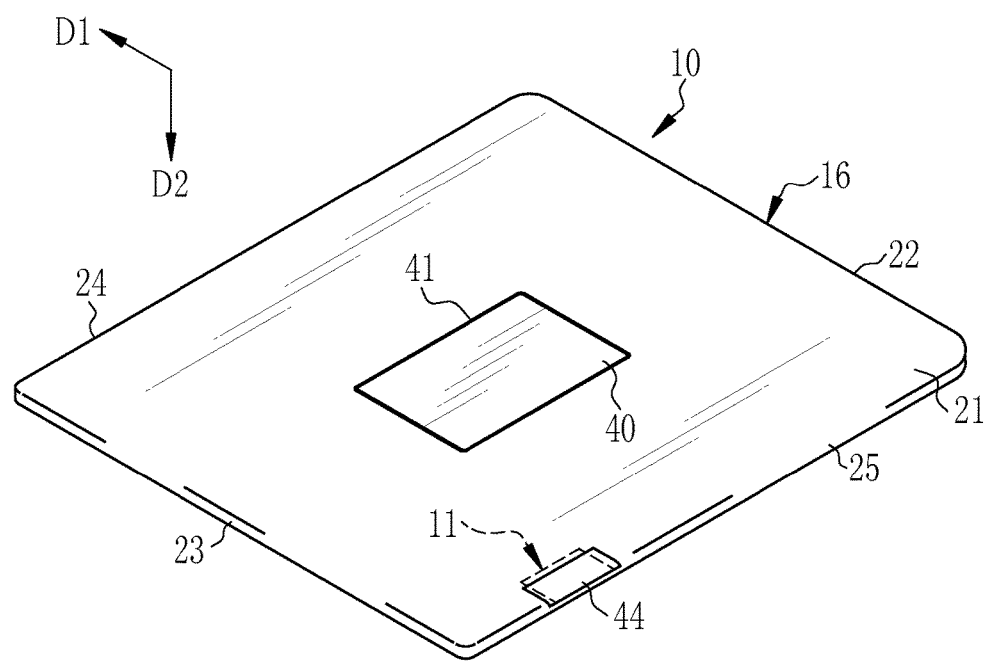
FIG. 2 is a perspective view illustrating an external appearance of the electronic cassette as viewed from a rear side thereof.

A battery mounting section 41 is formed at the center position of the rear surface 21 as shown in FIG. 2. A battery 40 for supplying electricity to activate the electronic cassette 10 is detachably mounted on the battery mounting section 41. FIG. 2 shows a state that the battery 40 is mounted on the battery mounting section 41.

The battery mounting section 41 is a concave portion in which the rear surface 21 is recessed toward the front surface 20. The battery mounting section 41 is formed to have the same planar shape and the same planar size as those of the battery 40, such that the battery 40 is fit into the battery mounting section 41 substantially without a gap. Additionally, the depth of the battery mounting section 41 from the rear surface 21 is substantially the same as the thickness of the battery 40. Therefore, in the state that the battery 40 is mounted on the battery mounting section 41 as shown in FIG. 2, an upper surface of the battery 40 is exposed through the rear surface 21, and the upper surface of the battery 40 and the rear surface 21 are on the same plane.

The electronic cassette 10 includes a control device (not shown) for controlling the operation of the electronic cassette 10, an antenna for generating a radio wave for wireless communication of various kinds of information such as X-ray images, and an oscillation circuit (not shown). In the case where such a wireless communication function is used, the electronic cassette 10 is activated by the electricity from the battery 40, namely, the electronic cassette 10 can be used without a cable.

Further, the electronic cassette 10 includes a female connector 11 which functions for wired communication with the control device. During the use of the wireless communication function, the female connector 11, to which the male connector 12 is not connected, is covered and protected by a lid 44.

The electronic cassette 10 receives not only the various kinds of information but also electricity through the female connector 11 from the control device. In the case where the female connector 11 and the male connector 12 are connected to each other, the electronic cassette 10 is activated by the electricity from the control device. It is also possible to charge the battery 40 with use of the electricity from the control device.

Figure 3:
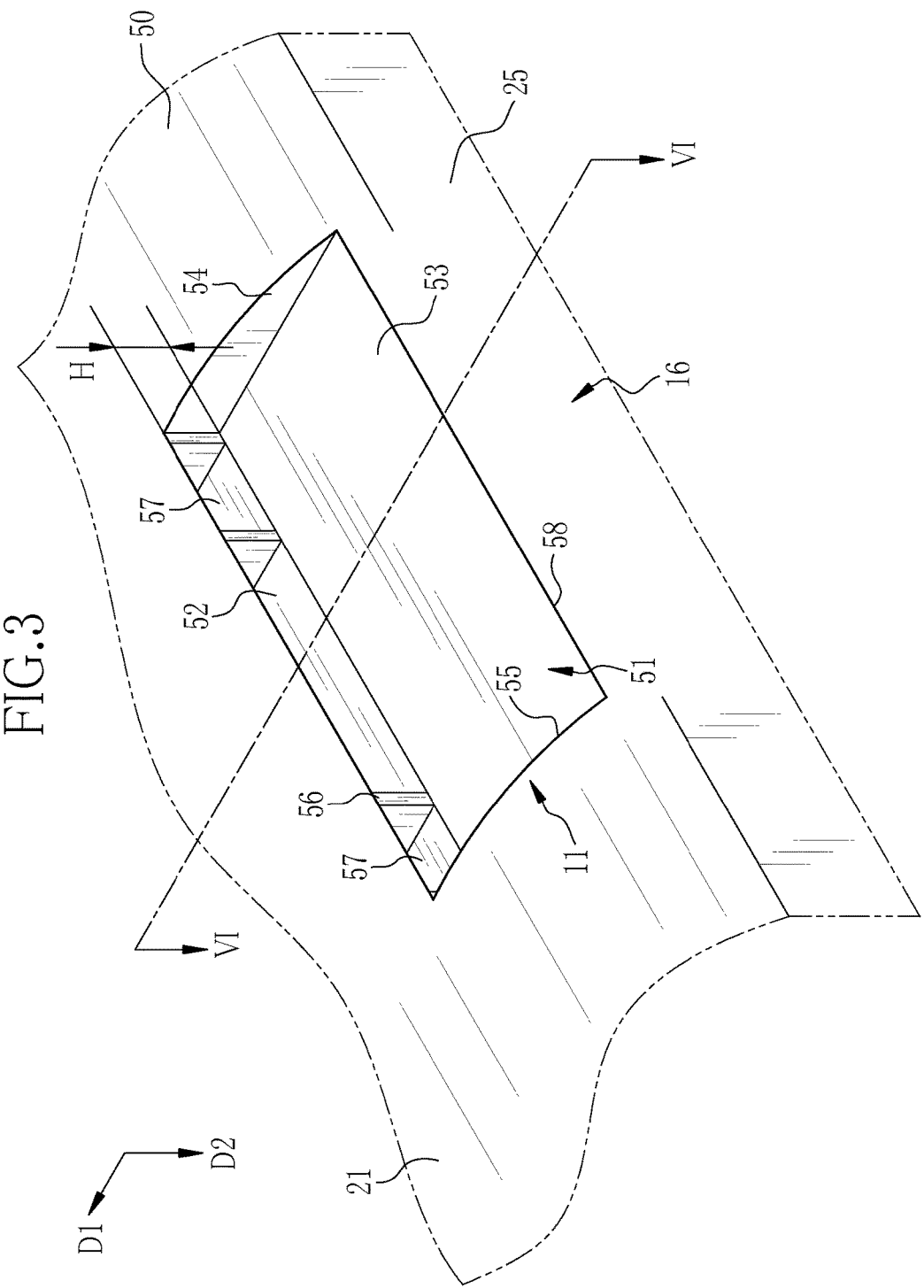
FIG. 3 is a perspective view illustrating an external appearance of a female connector.

FIG. 3 shows the surroundings of the female connector 11 from which the lid 44 is detached. As shown in FIG. 3, an inclined surface 50, which is inclined relative to the side surface 25 and the rear surface 21, is formed between the side surface 25 and the rear surface 21 (also see FIG. 6). The female connector 11 is formed on the inclined surface 50. The female connector 11 includes a fitting section 51 and a terminal 52 (hereinafter referred to as female terminal 52 to be distinguished from a terminal 65 of the male connector 12 (see FIG. 4)). The fitting section 51 consists of a first surface 53, a second surface 54, a third surface 55, a fourth surface 56, and engaging holes 57. The first surface 53 is formed along a direction D1 parallel to the front surface 20 and the rear surface 21 (also see FIGS. 1 and 2). The second surface 54, the third surface 55, and the fourth surface 56 respectively rise from three sides of the first surface 53 in a thickness direction D2 of the housing 16 (also see FIGS. 1 and 2). The fourth surface 56 is parallel to the side surface 25 of the housing 16, and located at a back side of the fitting section 51 in an insertion direction of the male connector 12. In this case, the direction for inserting the male connector 12 into the female connector 11 is the direction D1.

The female terminal 52 is disposed at the center position of the fourth surface 56. The engaging hole 57 is formed at both sides of the female terminal 52. Incidentally, the female terminal 52 and the engaging holes 57 may be formed on the first surface 53. In this case, the direction for inserting the male connector 12 into the female connector 11 is the direction D2. However, the state that the male connector 12 is fit into the female connector 11 after completion of the insertion is the same between the case where the insertion direction of the male connector 12 is the direction D1 and the case where the insertion direction of the male connector 12 is the direction D2.

An edge between the inclined surface 50 and each of the first surface 53 to the fourth surface 56 shown by a thick line in FIG. 3 constitutes an insertion port 58 into which a terminal section 61 (see FIG. 4) of the male connector 12 is inserted. Since the female connector 11 is formed on the inclined surface 50, the insertion port 58 extends toward the rear surface 21 of the housing 16 to a large extent.

Figure 4:
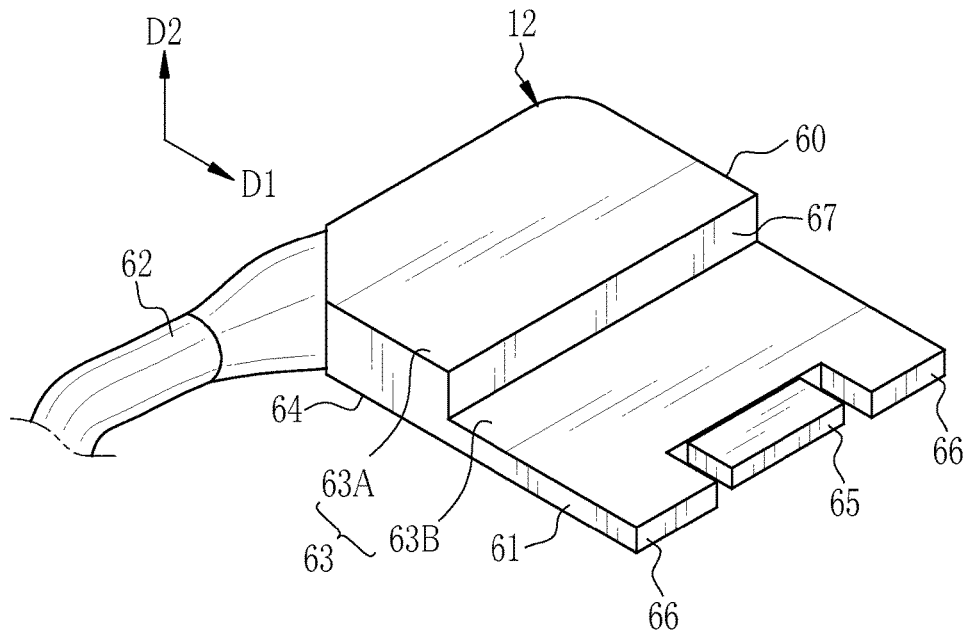
FIG. 4 is a perspective view illustrating an external appearance of a male connector.

As shown in FIG. 4, the male connector 12 consists of a main section 60 and the terminal section 61. One end of a cable 62 for connecting the electronic cassette 10 to a control device as one example of another device in a wired manner is connected to the main section 60. The other end of the cable 62 is connected to a connector (not shown) connected to the control device. The cable 62 is attached to a posterior end of the main section 60 so as to be opposed to the terminal section 61.

A planar shape of the male connector 12 as viewed from the front surface 20 of the housing 16 is substantially rectangular. In a state of being connected to the female connector 11, the male connector 12 has a first surface 63 facing the front surface 20, and a second surface 24 facing the rear surface 21. Each of the first surface 63 and the second surface 64 is parallel to the direction D1, and is perpendicular to the direction D2. The first surface 63 is divided into a surface 63A on the main section 60 side and a surface 63B on the terminal section 61 side. There is a step at a border between the main section 60 and terminal section 61 at the side of the front surface 20. The surface 60B is lower by one step than the surface 60B in the direction D2. In contrast, there is no step at the border between the main section 60 and terminal section 61 at the side of the rear surface 21. Namely, the main section 60 and terminal section 61 are connected to each other by the second surface 64 that is a flat surface. In the case where the female connector 11 and the male connector 12 are connected to each other, the surface 63B of the first surface 63 on the terminal section 61 side faces the first surface 53, and the second surface 64 is substantially entirely exposed to the outside.

Figure 7:
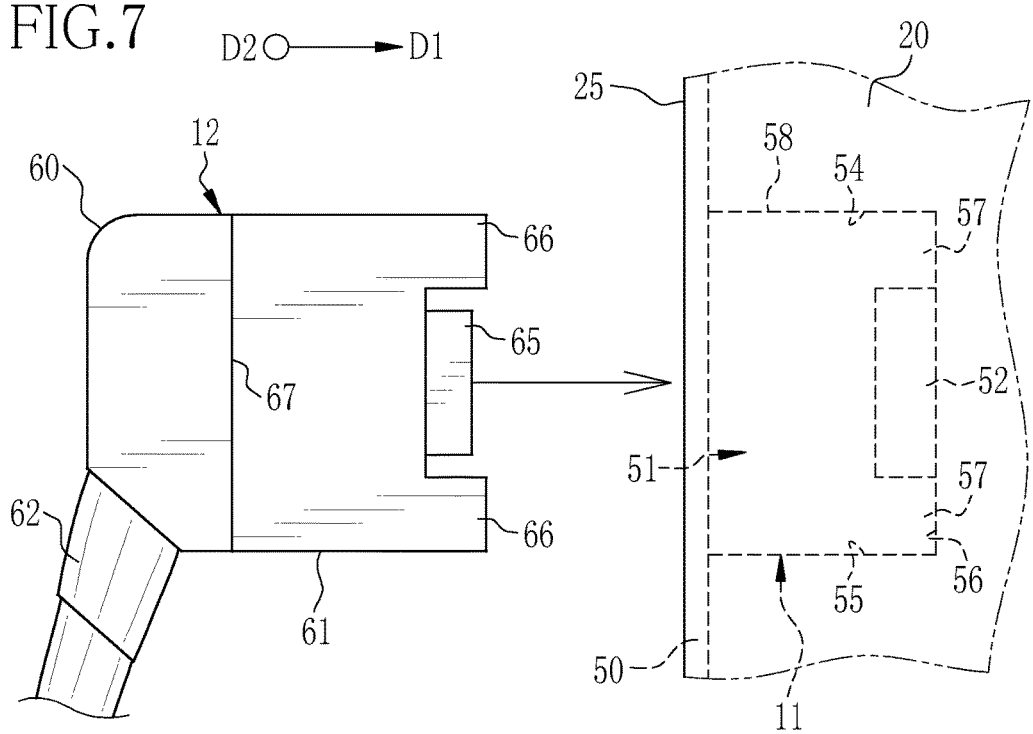
FIG. 7 is a view showing a state before the female connector and the male connector are connected to each other.
Figure 8:
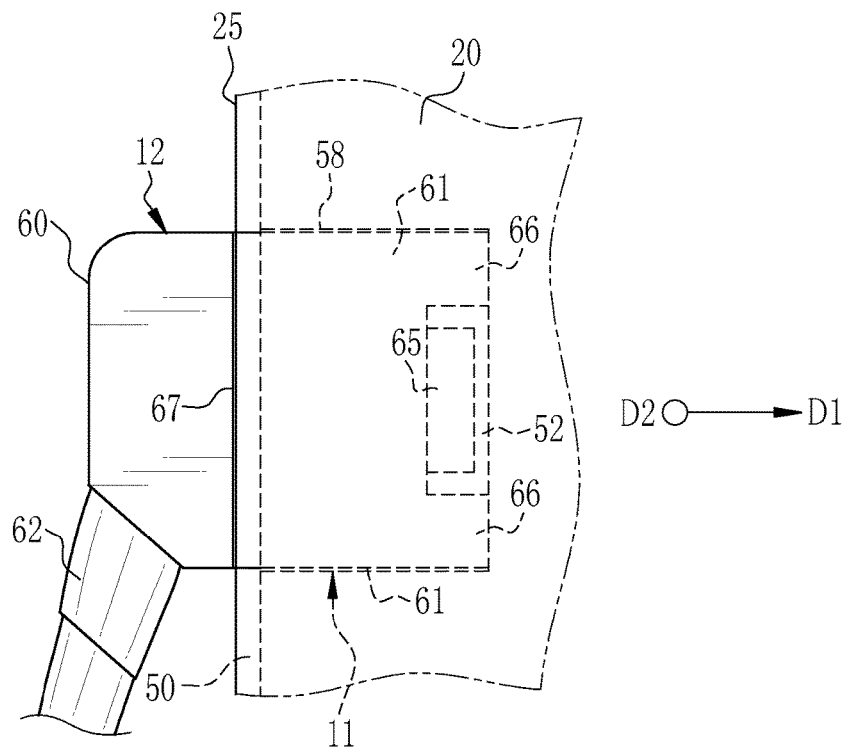
FIG. 8 is a view showing a state that the female connector and the male connector are connected to each other.

The terminal section 61 is fit into the fitting section 51 of the female connector 11 (see FIGS. 7 and 8). A terminal 65 (hereinafter referred to as male terminal 65) is disposed at the center position of a distal end of the terminal section 61. The male terminal 65 is fit into the female terminal 52 of the female connector 11, and electrically connected to the female terminal 52. An engaging protrusion 66 is formed at both sides of the male terminal 65. Each of the engaging protrusions 66 is engaged with the corresponding engaging hole 57 of the female connector 11. The engaging protrusions 66 serve as a positioning section for fitting the terminal section 61 into the fitting section 51 and as an auxiliary engaging section for securing the stable connection state between the female terminal 52 and the male terminal 65.

Figure 5:
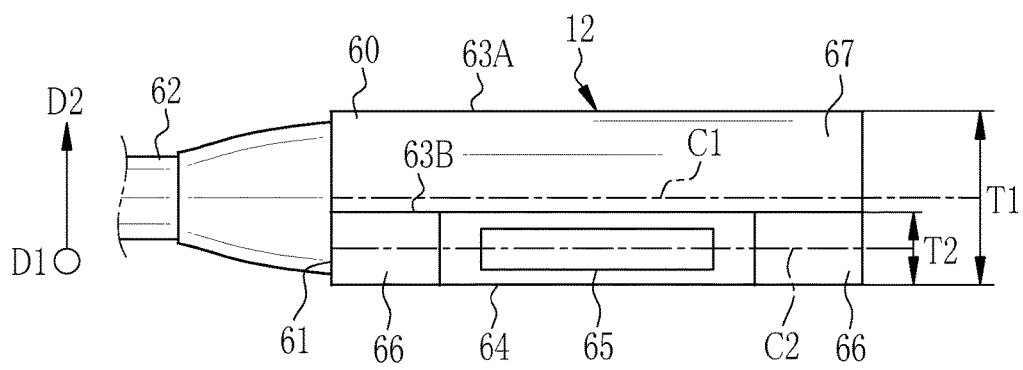
FIG. 5 is a plan view illustrating the external appearance of the male connector.

FIG. 5 shows the male terminal 12 as viewed from the terminal section 61. In FIG. 5, a thickness T1 of the main section 60 in the direction D2 is substantially the same as a diameter of a cross section of the cable 62 in the direction D2, such that one end the cable 62 is connected to the main section 60 of the male connector 12. Further, a thickness T2 of the terminal section 61 in the direction D2 is the same as a height H of the female connector 11 (i.e., height of the fourth surface 56 of the fitting section 51) in the direction D2 (see FIG. 3).

The thickness T2 of the terminal section 61 is smaller than the thickness T1 of the main section 60 (i.e., T2<T1). Further, a center position of the terminal section 61 shown by a dashed-dotted line denoted by the reference numeral C2 is located near to the rear surface 21 compared with a center position of the main section 60 shown by a dashed-dotted line denoted by the reference numeral C1 in the direction D2. Furthermore, as described above, the main section 60 and terminal section 61 are connected to each other by the flat second surface 64 at the side of the rear surface 21. The center position C1 of the main section 60 is located at a position which divides the thickness T1 of the main section 60 in half in the direction D2. The center position C2 of the terminal section 61 is located at a position which divides the thickness T2 of the terminal section 61 in half in the direction D2. In the case where the female terminal 52 and the engaging holes 57 are formed on the first surface 53, the male terminal 65 and the engaging protrusions 66 are formed on the surface 63B, and each of the male terminal 65 and the engaging protrusions 66 protrudes from the terminal section 61 toward the front surface 20 so as to have a convex shape. In this case, the thickness T2 is a thickness of the terminal section 61 excluding the thickness of the male terminal 65 having the convex shape and the thickness of the engaging protrusions 66 having the convex shape. Incidentally, to be exact, the reference numeral C1 denotes the dashed-dotted line passing through the center position of the main section 60. However, for convenience of explanation, in the case of describing "the center position of the main section 60", the reference numeral C1 is assigned such that "the center position of the main section 60" is referred to as "the center position C1 of the main section 60" as described above. Similarly, the center position of the terminal section 61, and a center position of the housing 16 and a center position of the female connector 11 which are described later, are described by being assigned with the reference numerals C2, C3, and C4, respectively.

It is possible to form the female terminal 52 and the engaging holes 57 on the first surface 53 and form the male terminal 65 and the engaging protrusions 66 on the surface 63B as described above. However, it is preferable that the female terminal 52 and the engaging holes 57 are formed on the fourth surface 56 and the male terminal 65 and the engaging protrusions 66 are formed at the distal end of the terminal section 61, such that the surface 63B is not convex but flat, as with this embodiment. This is because, according to this embodiment, the male connector 12 can be inserted into the female connector 11 in the direction D1, even in the case where the electronic cassette 10 is set to the holder of the upright radiographic stand or the supine radiographic stand, or put on a bed, and thereby the rear surface 21 is blocked.

Due to the above configuration, a step is formed at a border between the surface 63A of the main section 60 and the surface 63B of the terminal section 61, such that an end surface 67 parallel to the direction D2 is formed. Accordingly, the male connector 12 as viewed from a drawing direction of the cable 62 has a L-shape. The end surface 67 faces the side surface 25 of the housing 16 upon connection of the male connector 12 to the female connector 11 (see FIG. 8).

Note that, the thickness T1 of the main section 60 in the direction D2 is the maximum distance between the surface 63A and the second surface 64 in the direction D2. The thickness T2 of the terminal section 61 in the direction D2 is the maximum distance between the surface 63B and the second surface 64 in the direction D2.

FIG. 6 is a cross-sectional view of the housing 16 taken along a line VI-VI of FIG. 3, and shows a state that the outer grid 13 is attached to the housing 16. As shown in FIG. 6, the side panel 33 of the outer grid 13 has a length L that is a distance from the front surface 20 to a center position C3 of the housing 16 in the direction D2, for example, in order to facilitate the positioning of the outer grid 13 relative to the housing 16. Therefore, in the case where the outer grid 13 is attached to the housing 16, the side surface 25 is covered by the side panel 33 having the length L.

A center position C4 of the female connector 11 in the direction D2 is located near to the rear surface 21 compared with the center position C3 of the housing 16, so as to prevent the female connector 11 from being covered by the side panel 33 and avoid a situation that the male connector 12 cannot be connected to the female connector 11. The center position C3 of the housing 16 is located at a position which divides the thickness T3 of the housing 16 in half in the direction D2. An extended line of a line passing through the center position C3 of the housing 16 is perpendicular to the side surface 25 in this embodiment. The thickness T3 of the housing 16 is the maximum distance between the front surface 20 and the rear surface 21 in the direction D2. Further, the center position C4 of the female connector 11 is located at a position which divides the height H of the female connector 11 in half in the direction D2.

For example, the rear surface 21 is partially concave due to the battery mounting section 41 and the like. The maximum distance does not mean a distance between the surfaces having such partial concave portions and protrusions. The maximum distance means a distance between the surfaces having no partial concave portions and protrusions. According to this embodiment, the first surface 63 and the second surface 64 of the male connector 12 do not have partial concave portions and protrusions. However, even in the case where the first surface 63 and the second surface 64 of the male connector 12 have partial concave portions and protrusions, each of the thickness T1 of the main section 60 and the thickness T2 of the terminal section 61 is a distance between the first surface 63 and the second surface 64 each having no partial concave portions and protrusions.

Further, the height H of the female connector 11 in the state that the female connector 11 and the male connector 12 are connected to each other is the maximum distance between the surface of the female connector 11 facing the first surface 63 (e.g., the first surface 53 facing the surface 63A in this embodiment) and the surface of the female connector 11 facing the second surface 64 (e.g., a fifth surface 75 in a comparative example shown in FIG. 9) in the direction D2. In the case where the female connector 11 does not have a surface facing the second surface 64 as with this embodiment, the height H of the female connector 11 in the state that the female connector 11 and the male connector 12 are connected to each other is the maximum distance between the surface of the female connector 11 facing the first surface 63 and the second surface 64 in the direction D2.

The reference numeral 70 denotes an inclined surface formed between the side surface 25 and the front surface 20 in the similar manner as the inclined surface 50. Each of the inclined surfaces 50 and 70 is a curved surface which is convex toward the outside of the housing 16. Incidentally, although not shown in the drawing, the inclined surface 50 is also formed between the rear surface 21 and the side surfaces 22 to 24, respectively, and the inclined surface 70 is also formed between the front surface 20 and the side surfaces 22 to 24, respectively, in the similar manner as the side surface 25.

Next, an operation of the above configuration is explained by referring to FIGS. 6 to 10.

FIG. 7 shows a state before the female connector 11 and the male connector 12 are connected to each other as viewed from the front surface 20 of the housing 16, and FIG. 8 shows a state that the female connector 11 and the male connector 12 are connected to each other as viewed from the front surface 20 of the housing 16. Incidentally, for the purpose of avoiding complexity of the drawing, the fitting section 51, the second surface 54, the third surface 55, the fourth surface 56, the engaging holes 57, and the like are not shown in FIG. 8.

In FIG. 7, in order to connect the male connector 12 to the female connector 11, the male connector 12 is inserted into the female connector 11 along the direction D1 from the side at which the side surface 25 is located. Upon insertion of the male connector 12 into the female connector 11 along the direction D1, the engaging protrusions 66 are fit into the engaging holes 57 and the male terminal 65 is fit into the female terminal 52 as shown in FIG. 8. Additionally, the side surface 25 of the housing 16 faces the end surface 67 substantially without a gap. Thus, the female connector 11 and the male connector 12 are connected to each other.

Figure 9:
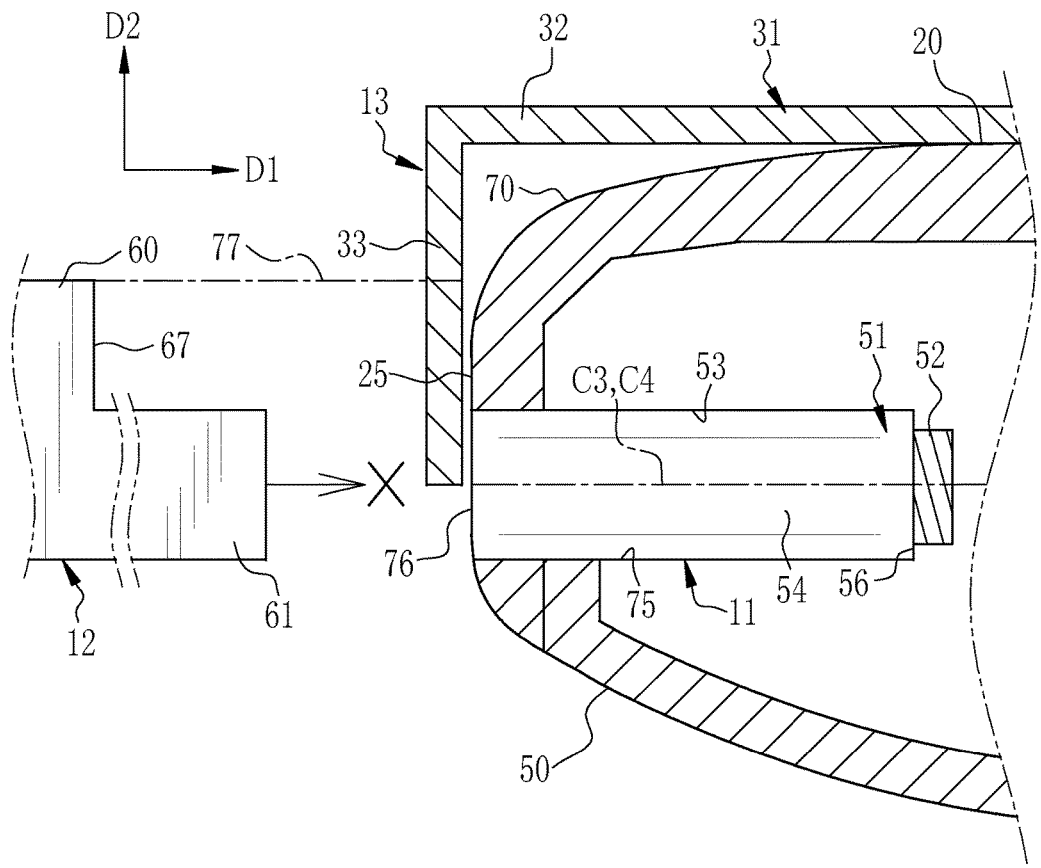
FIG. 9 is a view showing a comparative example in which a center position of the female connector is made coincident with a center position of a housing in a thickness direction of the housing.

Here, in the case where the center position C4 of the female connector 11 in the direction D2 is made coincident with the center position C3 of the housing 16 in the direction D2 as in the case of the comparative example shown in FIG. 9, an insertion port 76 of the female connector 11 is formed on the side surface 25. The fitting section 51 includes not only the first to fourth surfaces 53 to 56 but also a fifth surface 75 which faces and is parallel to the first surface 53. In the case where the female connector 11 and the male connector 12 are connected to each other, the fifth surface 75 faces the second surface 64. Further, an edge between the side surface 25 and each of the first surface 53 to the fourth surface 56 and the fifth surface 75 constitutes an insertion port 76. Since the insertion port 76 is formed on the side surface 25, the insertion port 76 has the same shape and the same size as those of the distal end of the terminal section 61.

In this case, for example, in the case where the outer grid 13 provided with the side panel 33 having the length L that is the distance between the front surface 20 and the center position C3 of the housing 16 as shown in FIG. 6 is attached to the housing 16, the female connector 11 (i.e., the insertion port 76) is covered by the side panel 33. Thus, the male connector 12 cannot be connected to the female connector 11. Therefore, only the outer grid 13 provided with the side panel 33 having a length corresponding to a distance between the front surface 20 and a dashed-dotted line denoted by the reference numeral 77 can be used, such that the side panel 33 does not cover the female connector 11 and does not come in contact with the main section 60. Alternatively, processing such as cutting out of part of the side panel 33 becomes necessary such that the side panel 33 has a length corresponding to the distance between the front surface 20 and the dashed-dotted line denoted by the reference numeral 77.

In contrast, according to this embodiment, the center position C4 of the female connector 11 is located near to the rear surface 21 compared with the center position C3 of the housing 16 in the direction D2. Therefore, it is possible to attach the outer grid 13 provided with the side panel 33 longer than the side panel 33 of the comparative example shown in FIG. 9 to the housing 16 without requiring any processing. Note that, in the comparative example shown in FIG. 9, the center position C4 of the female connector 11 in the direction D2 is made coincident with the center position C3 of the housing 16 in the direction D2. Specifically, it is possible to use the outer grid 13 provided with the side panel 33 having a length corresponding to the distance between the front surface 20 and a dashed-dotted line denoted by the reference numeral 78 shown in FIG. 6, such that the side panel 33 does not cover the female connector 11 and does not come in contact with the main section 60. Therefore, it becomes possible to use a greater variety of outer grids 13 without subjecting the outer grid 13 to any processing.

Furthermore, in the case where the female connector 11 is formed on the side surface 25 as with the comparative example shown in FIG. 9, the insertion port 76 has the same shape and the same size as those of the distal end of the terminal section 61. Therefore, it is necessary to precisely adjust the positions of the terminal section 61 and the insertion port 73 at the stage of inserting the terminal section 61 into the insertion port 76 and precisely adjust an insertion posture of the terminal section 61 relative to the direction D1. Accordingly, even in the case where the female connector 11 is not covered by the side panel 33 of the outer grid 13, it may be extremely difficult to connect the male connector 12 to the female connector 11.

Figure 10:
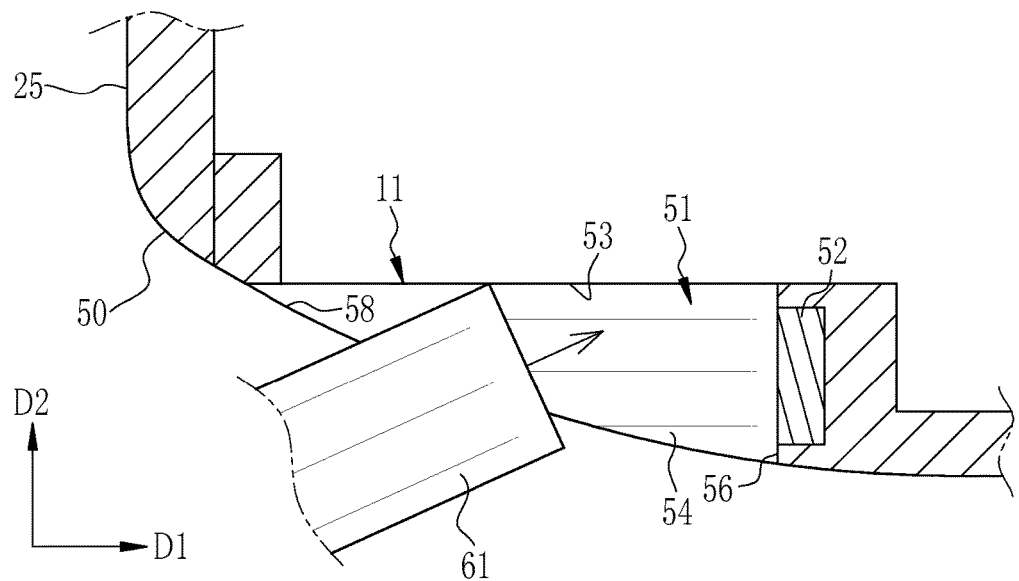
FIG. 10 is a view showing a state that a distal end of a terminal section is inserted into an insertion port.

In contrast, according to this embodiment, since the female connector 11 is formed on the inclined surface 50, the insertion port 58 extends toward the rear surface 21 to a large extent, and an opening area of the insertion port 58 is larger than that of the insertion port 76 shown in FIG. 9. Thus, it becomes easier for the insertion port 58 to receive the distal end of the terminal section 61. Additionally, in the case where the distal end of the terminal section 61 is inserted in a direction having a certain angle relative to the direction D1 as shown in FIG. 10, the distal end of the terminal section 61 is received by the first surface 53 of the fitting section 51. Then, while the distal end of the terminal section 61 is caused to move along the first surface 53 in the direction D1, the distal end of the terminal section 61 is guided by itself to the fourth surface 56 provided with the female terminal 52. Therefore, according to this embodiment, it is unnecessary to completely match the distal end of the terminal section 61 with the insertion port 58 at the stage of inserting the terminal section 61 into the insertion port 58. Additionally, it is unnecessary to completely adjust the insertion posture of the terminal section 61 relative to the direction D1. Therefore, it is possible to connect the male connector 12 to the female connector 11 without paying attention too much to the insertion angle of the male connector 12 relative to the female connector 11, and the usability is increased. Accordingly, in comparison with the comparative example shown in FIG. 9, it is easier to insert the terminal section 61, and it becomes possible to readily connect the male connector 12 to the female connector 11.

Further, the configuration of this embodiment, in which the insertion port 58 of the female connector 11 is formed on the inclined surface 50, is particularly effective in the case where the thickness T3 of the housing 16 is restricted by standards. This is because it is impossible to increase the thickness T3 of the housing 16 more than is necessary in the case where the thickness T3 of the housing 16 is restricted by the standards. Therefore, it is difficult to make the insertion port 76 larger in the configuration in which the insertion port 76 of the female connector 11 is formed on the side surface 25 as with the comparative example shown in FIG. 9. Thus, the insertion port 76 is forced to be small, and it becomes further difficult to insert the terminal section 61. Therefore, in the case where the thickness T3 of the housing 16 is restricted by the standards, it is extremely effective that the insertion port 58 is formed on the inclined surface 50.

Furthermore, since the thickness T2 of the terminal section 61 is made smaller than the thickness T1 of the main section 60, and the center position C2 of the terminal section 61 is located near to the rear surface 21 compared with the center position C1 of the main section 60 in the direction D2, it is possible to connect the male connector 12 to the female connector 11 having the center position C4 located near to the rear surface 21 while securing the thickness T1 of the main section 60 in accordance with the thickness of the cable 62.

Furthermore, since there is the step on the first surface 63 and the second surface 64 is flat, it is possible to distinguish a front side and a rear side of the male connector 12 at first sight. Thus, it is possible to prevent the male connector 12 from being connected to the female connector 11 in a state that the front side and the rear side of the male connector 12 are wrongly distinguished.

The provision of the inclined surfaces 50 and 70 allows the front surface 20, the rear surface 21, and the side surfaces 22 to 25 to be connected to each other by a smoothly curved surface having no corner. Therefore, the sense of touch with the housing 16 for the subject becomes softer. Further, in the case where the electronic cassette 10 is placed on a flat surface, it is possible to lift up the electronic cassette 10 easily by putting a finger on the inclined surfaces 50 and 70. Additionally, it is possible to smoothly insert the electronic cassette 10 into a clearance between the subject lying on the bed and the bed, since each of the corners of the housing 16 is rounded due to the provision of the inclined surfaces 50 and 70.

Second Embodiment

According to the first embodiment described above, the side surface 25 of the housing 16 faces the end surface 67 substantially without a gap in the case where the female connector 11 and the male connector 12 are connected to each other. In this state, the outer grid 13 provided with the side panel 33 having a length equal to or longer than a length that makes the side panel 33 come in contact with the main section 60 cannot be used.

Figure 11:
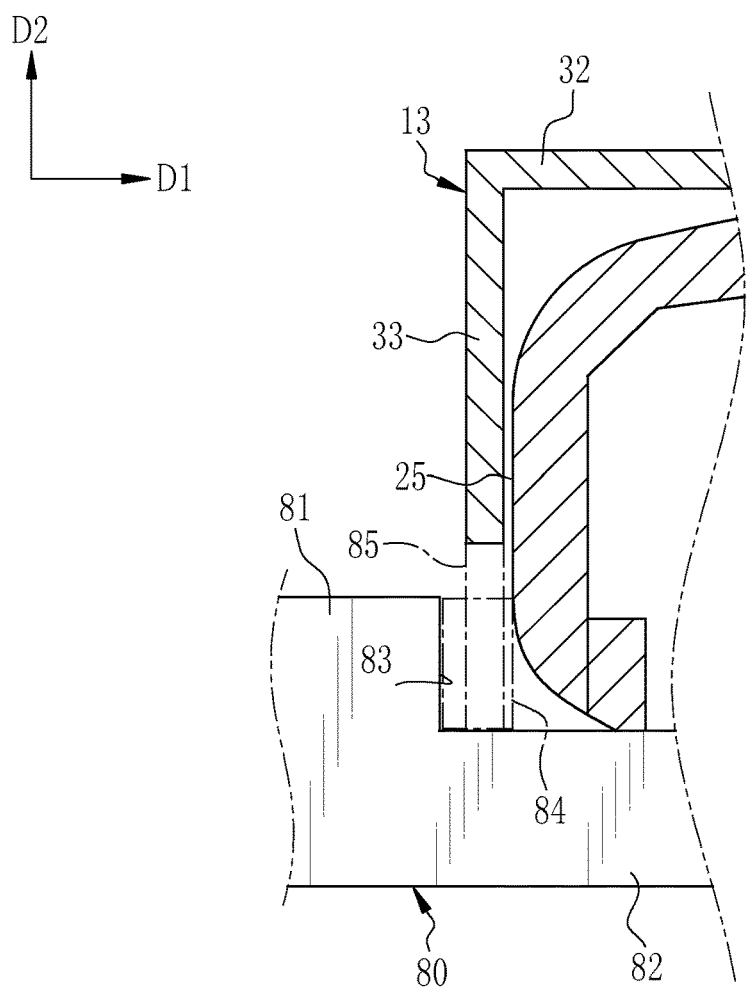
FIG. 11 is a view showing a second embodiment in which there is a gap having a size capable of receiving a side panel of a holding frame between an end surface of a male connector and a side surface of a housing.

Accordingly, in this embodiment, in order to increase the kinds of usable outer grids 13, in a state that a male connector 80 is connected to the female connector 11 as shown in FIG. 11, an end surface 83 is formed between a main section 81 and a terminal section 82 of the male connector 80, and a gap shown by a dashed-dotted line denoted by the reference numeral 84 is formed between the end surface 83 and the side surface 25. The gap 84 formed in the state that the female connector 11 and the male connector 80 are connected to each other has a size capable of receiving the side panel 33. Thereby, it is possible to use the outer grid 13 provided with the side panel 33 having a length shown by a dashed-dotted line denoted by the reference numeral 85 so as not to cover the female connector 11.

Figure 12:
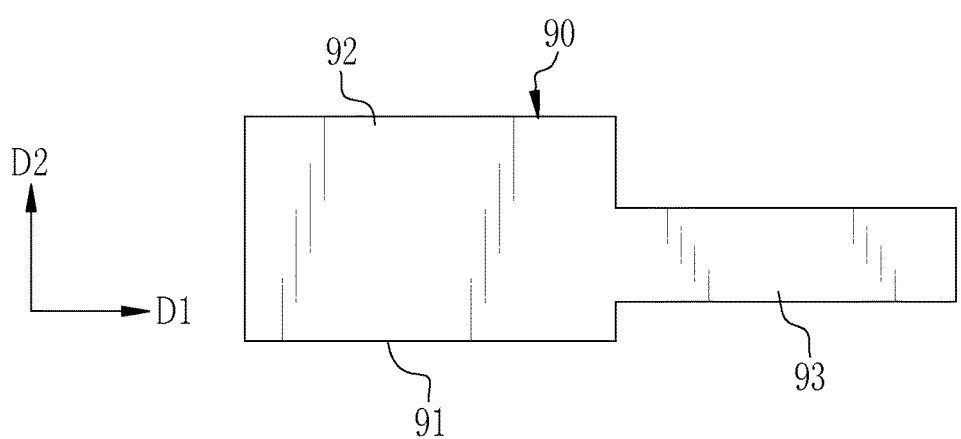
FIG. 12 is a view showing a male connector in one example.
Figure 13:
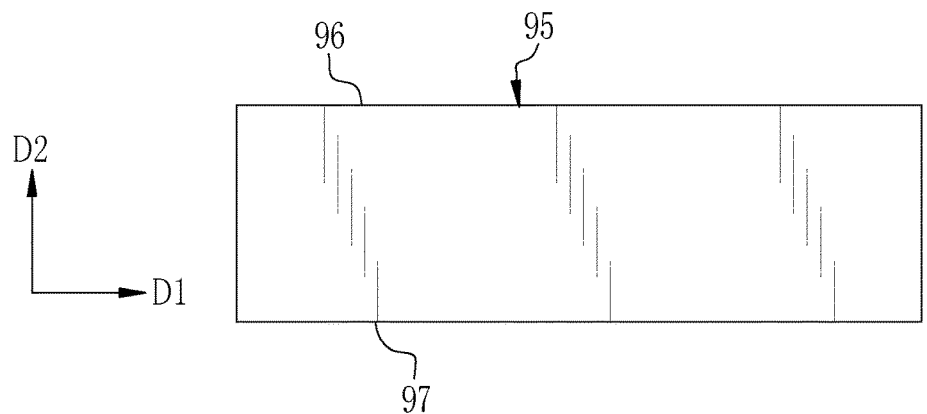
FIG. 13 is a view showing a male connector in another example.

Note that, the shape of the male connector 12 is not limited to that described in the first embodiment. For example, like a male connector 90 as shown in FIG. 12, a second surface 91 of a main section 92 may not be flat, and a step may be formed at a border between the second surface 91 and the terminal section 93. Further, like a male connector 95 shown in FIG. 13, each of a first surface 96 and a second surface 97 may be a flat surface, such that a main section and a terminal section constitute a flat plate in which the main section and the terminal section are not distinguished from each other. In this case, since a front side and a rear side of the male connector 95 cannot be determined by its appearance, a mark for indicating the front or rear side of the male connector 95 is put on the first surface 96 or the like.

Figure 14:
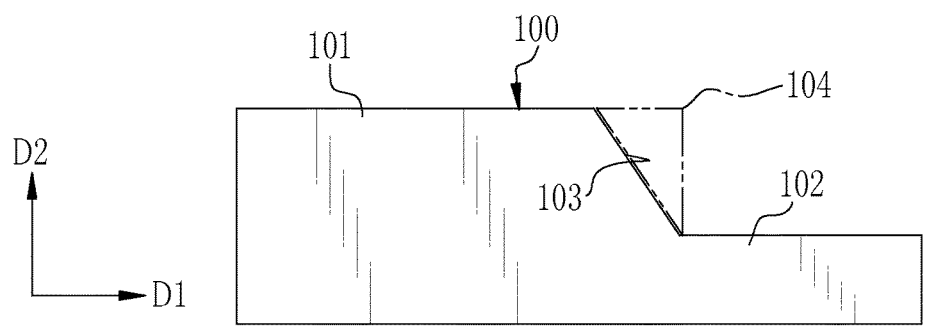
FIG. 14 is a view showing a male connector in still another example.

Furthermore, like a male connector 100 shown in FIG. 14, a main section 101 and a terminal section 102 may be connected by an inclined end surface 103, such that a gap 104 capable of receiving the side panel 33, which is shown by a dashed-dotted line, may be secured. Incidentally, the end surface 103 may be a flat surface as shown in FIG. 14, or a curved surface recessed toward the main section 101, for example.

Figure 15:
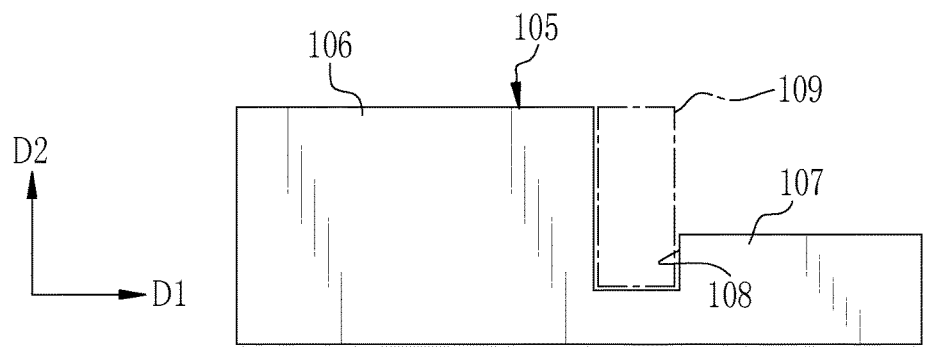
FIG. 15 is a view showing a male connector in yet another example.

Further, like a male connector 105 as shown in FIG. 15, a groove 108 may be formed between a main section 106 and a terminal section 107, such that a gap 109 capable of receiving the side panel 33, which is shown by a dashed-dotted line, may be secured. Although the strength of the male connector 105 is decreased due to the existence of the groove 108, the length of the gap 109 can be made longer.

Although the inclined surface 50 is formed between the rear surface 21 and each of the side surfaces 22 to 25 in the first embodiment, it is sufficient that the inclined surface 50 is formed at least between the rear surface 21 and the side surface 25 provided with the female connector 11.

The side panel of the outer grid is not necessarily provided for all the side surfaces 22 to 25. For example, an outer grid which is not provided with a side panel facing the side surface 23 may be used. Further, each of the inclined surfaces 50 and 70 is not limited to the curved surface which is convex toward the outside of the housing 16 as described in the first embodiment, and may be a flat surface or may be in a shape obtained by combining a curved surface and a flat surface.

Note that, it is sufficient that the electronic cassette system includes at least the electronic cassette and the male connector to be connected to the female connector. Further, without using the scintillator, a direct conversion-type image detector using a conversion layer (amorphous selenium or the like) which directly converts the X-ray into the charge may be used. Furthermore, although the image detector of the TFT type is exemplified in the above embodiments, the present invention may adopt an image detector of a CMOS (Complementary Metal Oxide Semiconductor) type. Further, the present invention is also applicable to an electronic cassette system and an electronic cassette using other radiation rays such as γ-rays instead of the X-rays in radiography.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic cassette system comprising:
   an electronic cassette including an image detector and a housing for housing the image detector, the image detector detecting a radiation image of a subject based on radiation having been transmitted through the subject, and the housing having a front surface on which the radiation is incident, a rear surface facing the front surface, and four side surfaces;
   a female connector disposed in the housing; and
   a male connector to be connected to the female connector, the male connector extending from a side-surface side of the housing in a direction parallel to the front surface and the rear surface of the housing, wherein
   a center position of the female connector is located closer to the rear surface of the housing compared with a center position of the housing in a thickness direction of the housing perpendicular to the front surface and the rear surface,
   the housing has an inclined surface which is formed at least between one of the side surfaces and the rear surface and inclined relative to the one of the side surfaces and the rear surface, and
   the female connector includes an insertion port configured to open only in the inclined surface and to receive an insertion of the male connector.

2. The electronic cassette system according to claim 1, wherein
   the male connector includes a main section to which one end of a cable for connecting the electronic cassette to another device in a wired manner is connected, and a terminal section having a terminal which is fit into the female connector to establish an electrical connection between the electronic cassette and the device,
   the terminal section is thinner than the main section in the thickness direction of the housing, and
   a center position of the terminal section is located closer to the rear surface of the housing compared with a center position of the main section in the thickness direction of the housing.

3. The electronic cassette system according to claim 1, further comprising an outer grid detachably attached to the housing externally, the outer grid removing scattered rays generated upon transmission of the radiation through the subject.

4. The electronic cassette system according to claim 2, wherein the main section and the terminal section are connected to each other by a flat surface on a rear-surface side of the housing.

5. The electronic cassette system according to claim 2, wherein a gap is provided between an end surface which is formed between the main section and the terminal section and a surface of the housing which faces the end surface upon connection of the male connector to the female connector by fitting the terminal section into the female connector.

6. The electronic cassette system according to claim 3, wherein the outer grid including:
   a top panel for covering the front surface of the housing; and
   a side panel which is provided to an edge of the top panel and extends in a direction from a front-surface side to a rear-surface side of the housing so as to cover part of the side surface of the housing.

7. The electronic cassette system according to claim 6, wherein
   a gap is provided between an end surface which is formed between a main section and a terminal section and a surface of the housing which faces the end surface upon connection of the male connector to the female connector by fitting the terminal section into the female connector, and
   the gap has a size to receive the side plate.

8. An electronic cassette comprising:
   an image detector for detecting a radiation image of a subject based on radiation having been transmitted through the subject;
   a housing for housing the image detector, the housing having a front surface on which the radiation is incident, a rear surface facing the front surface, and four side surfaces; and
   a female connector disposed in the housing, the female connector being connected to a male connector extending from a side-surface side of the housing in a direction parallel to the front surface and the rear surface of the housing, wherein
   a center position of the female connector is located closer to the rear surface of the housing compared with a center position of the housing in a thickness direction of the housing perpendicular to the front surface and the rear surface,
   the housing has an inclined surface which is formed at least between one of the side surfaces and the rear surface and inclined relative to the one of the side surfaces and the rear surface, and
   the female connector includes an insertion port configured to open only in the inclined surface and to receive an insertion of the male connector.

* * * * *